(12) United States Patent
Besner et al.

(10) Patent No.: US 8,093,213 B2
(45) Date of Patent: Jan. 10, 2012

(54) HEPARIN BINDING EPIDERMAL GROWTH FACTOR (HB-EGF) FOR USE IN METHODS OF TREATING AND PREVENTING INTESTINAL INJURY RELATED TO HEMORRHAGIC SHOCK AND RESUSCITATION

(75) Inventors: Gail E. Besner, Dublin, OH (US); Osama N. El-Assal, Gahanna, OH (US)

(73) Assignee: Nationwide Children's Hospital, Inc., Columbus, OH (US)

( * ) Notice: Subject to any disclaimer, the term of this patent is extended or adjusted under 35 U.S.C. 154(b) by 0 days.

(21) Appl. No.: 12/598,082

(22) PCT Filed: Apr. 28, 2008

(86) PCT No.: PCT/US2008/061772
§ 371 (c)(1),
(2), (4) Date: Apr. 26, 2010

(87) PCT Pub. No.: WO2008/134635
PCT Pub. Date: Nov. 6, 2008

(65) Prior Publication Data
US 2010/0222265 A1  Sep. 2, 2010

Related U.S. Application Data

(60) Provisional application No. 60/914,997, filed on Apr. 30, 2007.

(51) Int. Cl.
*A61K 38/18* (2006.01)
(52) U.S. Cl. .......................................................... 514/9.6
(58) Field of Classification Search ........................ None
See application file for complete search history.

(56) References Cited

U.S. PATENT DOCUMENTS

| | | | |
|---|---|---|---|
| 5,057,494 A | 10/1991 | Sheffield | |
| 5,811,393 A | 9/1998 | Klagsbrun et al. | |
| 5,990,153 A | 11/1999 | Wood et al. | |
| 6,191,109 B1 | 2/2001 | Besner et al. | |
| 6,387,878 B1 | 5/2002 | Besner et al. | |
| 7,361,638 B2 * | 4/2008 | Acosta et al. | 514/11.4 |
| 2003/0186865 A1 * | 10/2003 | Acosta et al. | 514/12 |
| 2006/0019898 A1 | 1/2006 | Besner et al. | |

FOREIGN PATENT DOCUMENTS

WO   WO-92/06705   4/1992

OTHER PUBLICATIONS

Barnard et al., Epidermal growth factor-related peptides and their relevance to gastrointestinal pathophysiology, *Gastroenterology*, 108:564-80 (1995).
Bell et al., The microbial flora and antimicrobial therapy of neonatal peritonitis, *J. Ped. Surg.*, 15:569 (1980).
Besner et al., Interaction of heparin-binding EGF-like growth factor (HB-EGF) with the epidermal growth factor receptor: Modulation by heparin, heparinase, or synthetic heparin-binding HB-EGF fragments, *Growth Factors*, 7:289-96 (1992).
Besner et al., Isolation and characterization of a macrophage-derived heparin-binding growth factor, *Cell Regulation*, 1:811-9 (1990).
Carey et al., Molecular cloning and characterization of N-syndecan, a novel transmembrane heparan sulfate proteoglycan, *J. Cell. Biol.*, 117(1):191-201 (1992).
Dignass et al., Cytokine modulation of intestinal epithelial cell resitution: Cental role of transforming growth factor β, *Gastroenterology*, 105:1323-32 (1993).
Feng et al., Heparin-binding epidermal growth factor-like growth factor decreases the incidence of necrotizing enterocolitis in neonatal rats. *J. Ped. Surg.* 41: 144-9 (2006).
Galvao et al., Epidermal growth factor (EGF) did not protect against renal ischemia, *J. Am Soc. Nephrol.*, 7(9): 1824 (1996).
Higashiyama et al., A heparin-binding growth factor secreted by macrophage-like cells that is related to EGF, *Science*, 251:936-9 (1991).
Killion et al., Exogenous epidermal growth factor fails to accelerate functional recovery in the autotransplanted ischemic pig kidney, *J. Urology*, 150: 1551-6 (1993).
Martin et al., Timing, route, and dose of administration of heparin-binding epidermal growth factor-like growth factor in protections against intestinal ischemia-reperfusion injury. *J. Ped. Surg.* 40(11): 1741-7 (2005).
Miyazaki et al., Oxidative stress increases gene expression of heparin-binding EGF-like growth factor and amphiregulin in cultured rat gastric epithelial cells, *Biochem. Biophys. Res. Comm.*, 226: 542-6 (1996).
Parks et al., Contributions of ischemia and reperfusion to mucosal lesion formation, *Am. J. Physiol.*, 250:G749-53 (1986).
Pillai et al., Heparin-binding epidermal growth factor-like growth factor protects rat intestine from ischemia/reperfusion injury. *J. Surg. Res.* 87(2): 225-31 (1999). Prigent et al., The type 1 (EGFR-related) family of growth factor receptors and their ligands, *Prog. Growth Factor Res.*, 4:1-24 (1992).
Robinson et al., Epidermal growth factor (hEGF) has no effect on murine intestine epithelial damage and regeneration after melphalan, *Br. J. Cancer*, 52: 733-7 (1985).
Villa et al., Epidermal growth factor reduces ischemia-reperfusion injury in rat small intestine, *Gastroenterology*, 110(4 Suppl.):A372 (1996).

* cited by examiner

*Primary Examiner* — Marianne P Allen
(74) *Attorney, Agent, or Firm* — Marshall, Gerstein & Borun LLP

(57) ABSTRACT

The invention is related to methods of protecting, preventing and reducing intestinal injury in a human subject suffering from or at risk for shock, hemorrhagic shock or hemorrhagic shock and resuscitation (HS/R) comprising administering heparin binding epidermal growth factor (HB-EGF). The invention is also related to methods of inhibiting deterioration of intestinal blood flow and methods of preserving and increasing intestinal blood flow by administering HB-EGF to a human subject. In addition, the methods of the invention should improve the clinical outcome of human subject suffering from or at risk for shock, hemorrhagic shock or hemorrhagic shock and resuscitation.

8 Claims, No Drawings

SEQUENCE LISTING

```
<160> NUMBER OF SEQ ID NOS: 2

<210> SEQ ID NO 1
<211> LENGTH: 624
<212> TYPE: DNA
<213> ORGANISM: Homo sapiens
<220> FEATURE:
<221> NAME/KEY: CDS
<222> LOCATION: (1)..(624)

<400> SEQUENCE: 1 atg aag ctg ctg ccg tcg gtg gtg ctg aag ctc ttt ctg gct gca gtt       48
Met Lys Leu Leu Pro Ser Val Val Leu Lys Leu Phe Leu Ala Ala Val
1               5                   10                  15 ctc tcg gca ctg gtg act ggc gag agc ctg gag cgg ctt cgg aga ggg       96
Leu Ser Ala Leu Val Thr Gly Glu Ser Leu Glu Arg Leu Arg Arg Gly
            20                  25                  30 cta gct gct gga acc agc aac ccg gac cct ccc act gta tcc acg gac      144
Leu Ala Ala Gly Thr Ser Asn Pro Asp Pro Pro Thr Val Ser Thr Asp
        35                  40                  45 cag ctg cta ccc cta gga ggc ggc cgg gac cgg aaa gtc cgt gac ttg      192
Gln Leu Leu Pro Leu Gly Gly Gly Arg Asp Arg Lys Val Arg Asp Leu
    50                  55                  60 caa gag gca gat ctg gac ctt ttg aga gtc act tta tcc tcc aag cca      240
Gln Glu Ala Asp Leu Asp Leu Leu Arg Val Thr Leu Ser Ser Lys Pro
65                  70                  75                  80 caa gca ctg gcc aca cca aac aag gag gag cac ggg aaa aga aag aag      288
Gln Ala Leu Ala Thr Pro Asn Lys Glu Glu His Gly Lys Arg Lys Lys
                85                  90                  95 aaa ggc aag ggg cta ggg aag aag agg gac cca tgt ctt cgg aaa tac      336
Lys Gly Lys Gly Leu Gly Lys Lys Arg Asp Pro Cys Leu Arg Lys Tyr
            100                 105                 110 aag gac ttc tgc atc cat gga gaa tgc aaa tat gtg aag gag ctc cgg      384
Lys Asp Phe Cys Ile His Gly Glu Cys Lys Tyr Val Lys Glu Leu Arg
        115                 120                 125 gct ccc tcc tgc atc tgc cac ccg ggt tac cat gga gag agg tgt cat      432
Ala Pro Ser Cys Ile Cys His Pro Gly Tyr His Gly Glu Arg Cys His
    130                 135                 140 ggg ctg agc ctc cca gtg gaa aat cgc tta tat acc tat gac cac aca      480
Gly Leu Ser Leu Pro Val Glu Asn Arg Leu Tyr Thr Tyr Asp His Thr
145                 150                 155                 160 acc atc ctg gcc gtg gtg gct gtg gtg ctg tca tct gtc tgt ctg ctg      528
Thr Ile Leu Ala Val Val Ala Val Val Leu Ser Ser Val Cys Leu Leu
```

-continued

```
                                165                 170                 175
gtc atc gtg ggg ctt ctc atg ttt agg tac cat agg aga gga ggt tat          576
Val Ile Val Gly Leu Leu Met Phe Arg Tyr His Arg Arg Gly Gly Tyr
            180                 185                 190 gat gtg gaa aat gaa gag aaa gtg aag ttg ggc atg act aat tcc cac          624
Asp Val Glu Asn Glu Glu Lys Val Lys Leu Gly Met Thr Asn Ser His
            195                 200                 205

<210> SEQ ID NO 2
<211> LENGTH: 208
<212> TYPE: PRT
<213> ORGANISM: Homo sapiens

<400> SEQUENCE: 2

Met Lys Leu Leu Pro Ser Val Val Leu Lys Leu Phe Leu Ala Ala Val
1               5                   10                  15

Leu Ser Ala Leu Val Thr Gly Glu Ser Leu Glu Arg Leu Arg Arg Gly
                20                  25                  30

Leu Ala Ala Gly Thr Ser Asn Pro Asp Pro Thr Val Ser Thr Asp
            35                  40                  45

Gln Leu Leu Pro Leu Gly Gly Gly Arg Asp Arg Lys Val Arg Asp Leu
    50                  55                  60

Gln Glu Ala Asp Leu Asp Leu Leu Arg Val Thr Leu Ser Ser Lys Pro
65                  70                  75                  80

Gln Ala Leu Ala Thr Pro Asn Lys Glu Glu His Gly Lys Arg Lys Lys
                85                  90                  95

Lys Gly Lys Gly Leu Gly Lys Lys Arg Asp Pro Cys Leu Arg Lys Tyr
            100                 105                 110

Lys Asp Phe Cys Ile His Gly Glu Cys Lys Tyr Val Lys Glu Leu Arg
        115                 120                 125

Ala Pro Ser Cys Ile Cys His Pro Gly Tyr His Gly Glu Arg Cys His
    130                 135                 140

Gly Leu Ser Leu Pro Val Glu Asn Arg Leu Tyr Thr Tyr Asp His Thr
145                 150                 155                 160

Thr Ile Leu Ala Val Val Ala Val Val Leu Ser Ser Val Cys Leu Leu
                165                 170                 175

Val Ile Val Gly Leu Leu Met Phe Arg Tyr His Arg Arg Gly Gly Tyr
            180                 185                 190

Asp Val Glu Asn Glu Glu Lys Val Lys Leu Gly Met Thr Asn Ser His
        195                 200                 205
```

HEPARIN BINDING EPIDERMAL GROWTH FACTOR (HB-EGF) FOR USE IN METHODS OF TREATING AND PREVENTING INTESTINAL INJURY RELATED TO HEMORRHAGIC SHOCK AND RESUSCITATION

This application is a national phase of International Application No. PCT/US2008/61772 filed Apr. 28, 2008, which claims the priority benefit of U.S. Provisional Patent Application No. 60/914,997.

FIELD OF INVENTION

The invention is related to methods of protecting, preventing and reducing intestinal injury in a human subject at risk for or suffering from shock, hemorrhagic shock (HS) or hemorrhagic shock and resuscitation (HS/R) comprising administering heparin binding epidermal growth factor (HB-EGF) to the subject. The invention is also related to methods of inhibiting deterioration of intestinal blood flow and methods of preserving and increasing intestinal blood flow by administering HB-EGF to a human subject. In addition, the methods of the invention should improve the clinical outcome of human subjects suffering from or at risk for shock, HS or HS/R.

BACKGROUND

HB-EGF was first identified in the conditioned medium of cultured human macrophages. It is synthesized as a transmembrane, biologically active precursor protein (proHB-EGF) composed of 208 amino acids, which is enzymatically cleaved by matrix metalloproteinases (MMPs) to yield a 14-20 kDa soluble growth factor (sHB-EGF). Pro-HB-EGF can form complexes with other membrane proteins including CD9 and integrin $\alpha 3\beta 1$; these binding interactions function to enhance the biological activity of pro-HB-EGF. ProHB-EGF is a juxtacrine factor that can regulate the function of adjacent cells through its engagement of cell surface receptor molecules.

sHB-EGF is a potent mitogenic and chemoattractant protein for many types of cells. Similar to all members of the EGF family, HB-EGF binds to the "classic" or prototypic epidermal growth factor receptor (EGFR; ErbB-1). However, while the mitogenic function of sHB-EGF is mediated through activation of ErbB-1, its migration-inducing function involves the activation of ErbB-4 and the more recently described N-arginine dibasic convertase (NRDc, Nardilysin). This is in distinction to other EGF family members such as EGF itself, transforming growth factor (TGF)-$\alpha$ and amphiregulin (AR), which exert their signal-transducing effects via interaction with ErbB-1 only. In fact, the NRDc receptor is totally HB-EGF-specific. In addition, unlike most members of the EGF family, which are non-heparin binding, sHB-EGF is able to bind to cell-surface heparin-like molecules (heparan sulfate proteoglycans; HSPG), which act as low affinity, high capacity receptors for HB-EGF. The differing affinities of EGF family members for the different EGFR subtypes and for HSPG may confer different functional capabilities to these molecules in vivo. The combined interactions of HB-EGF with HSPG and ErbB-1/ErbB-4/NRDc may confer a functional advantage to this growth factor.

Although the HB-EGF gene is widely expressed, the basal level of its mRNA is relatively low in normal cells. Expression of HB-EGF is significantly increased in response to tissue damage, hypoxia and oxidative stress, and also during wound healing and regeneration. This pattern of expression is consistent with a pivotal role for HB-EGF in ischemia/reperfusion (I/R) injury, regeneration, and repair processes.

Intestinal barrier function represents a critical initial defense against noxious intraluminal substances. Although the intestine is not as essential as the vital organs in the immediate preservation of life, I/R is as lethal as extensive heart and brain ischemia. The gut has a higher critical oxygen requirement compared to the whole body and other vital organs. Accordingly, the intestinal mucosa is extremely susceptible to I/R and even short periods of ischemia can initiate local and remote tissue damage as well as systemic hemodynamic disturbances.

Reactive oxygen species (ROS), pro-inflammatory cytokines, leukocyte adhesion, and complement activation can all mediate intestinal I/R. Loss of immune and barrier functions of the gut secondary to I/R leads to significant detrimental effects on other organs such as lungs, liver, kidneys and heart, and may result in multiple organ dysfunction syndrome (MODS) and death. Exploring the potential of new therapeutic strategies to enhance the regenerative capacity and/or increase the resistance of the intestine to I/R injury would improve outcome in these patients.

The gut is highly susceptible to hypoperfusion injury due to its higher critical oxygen requirement compared to the whole body, and due to the mucosal countercurrent microcirculation. Not surprisingly, patients subjected to hypoperfusion states such as hemorrhagic shock and resuscitation (HS/R), trauma, and major surgery often develop intestinal ischemia as documented by both experimental and clinical studies.

Following the hypoperfusion effects of the shock stage, traditional methods of resuscitation often fail to adequately restore mesenteric perfusion despite stabilization of heart rate, blood pressure, and improved perfusion in some organs such as the heart and brain. To the contrary, resuscitation is characterized by progressive deterioration of mesenteric blood flow. Progressive intestinal hypoperfusion after HS/R contributes to loss of the gut mucosal barrier and to hypoxia-induced intestinal inflammation, both of which are critical to the initiation of MODS after HS/R. Accordingly, factors that protect the intestine from injury and promote early intestinal healing by restitution could significantly improve outcome after HS/R.

HB-EGF has been demonstrated to be essential for intestinal healing by restitution in intestinal epithelial cells (IEC) in vitro and in rats subjected to superior mesenteric artery occlusion (SMAO) in vivo (El-Assal & Besner Gastroenterology 129(2): 609-625. 2005). These HB-EGF-induced effects are mediated via activation of various molecular mechanisms including MEK/ERK and PI3K/Akt signaling pathways.

A few reports have demonstrated the importance of HB-EGF in promoting endothelial cell (EC) functions including angiogenesis. Exogenous HB-EGF was shown to promote rabbit corneal angiogenesis and neovascularization in mouse skin (Abramovitch et al., FEBS Lett 425(3):441-7, 1998) and recent studies have shown that HB-EGF is involved in tumor angiogenesis (Ongusaha et al. Cancer Res 64(15):5283-90, 2004), catecholamine-induced vascular trophic effects (Zhang et al., Circ Res 95(10):989-97, 2004) and angiopoietin-induced angiogenesis (Iivanainen et al., Faseb J 17(12): 1609-21, 2003). HB-EGF belongs to the epidermal growth factor (EGF) family that functions via activation of the tyrosine kinase EGF receptor (EGFR). Another member of this family, EGF itself, has been shown to increase mesenteric blood flow in sheep and to induce direct relaxation of isolated rabbit mesenteric arteries via activation of EGFR. Further studies have demonstrated that the gastroprotective effects of EGF are mediated in part by its ability to increase gastric blood flow. To date, the effects of HB-EGF on mesenteric blood flow have not been elucidated.

Hemorrhagic shock (HS)—induced injuries and hemorrhagic shock and resuscitation (HS/R)—induced injuries are conditions that may result from any type of trauma or severe blood loss. Therefore, there is a continuing need to develop methods of preventing injuries due to HS or HS/R and therapeutic compositions for preventing and treating these intestinal injuries.

SUMMARY OF INVENTION

Factors that protect the intestine from HS and HS/R-induced injury and promote early intestinal healing by restitution may significantly improve the clinical outcome of human subjects suffering from HS or HS/R. Previous data has indicated that HB-EGF is essential for intestinal healing by restitution in intestinal epithelial cells. The present invention contemplates that HB-EGF may also protect the intestines from injury after HS or HS/R. The invention particularly provides for methods of treating subjects who are at risk for, or who are experiencing the early stages of HS/R by administering HB-EGF and thereby preventing, reducing or protecting the intestine from injury. The data presented herein evaluated the role of HB-EGF in preserving mesenteric blood flow and protecting the intestines from HS- or HS/R-induced injury.

The invention provides for methods of treating a human subject suffering from or at risk for HS or HS/R by administering a HB-EGF product. As demonstrated in Examples 1-6, HB-EGF protected intestinal epithelial cells and intestinal endothelial cells from HS- or HS/R-induced injury in a rat model of HS and HS/R. The invention contemplates administering HB-EGF immediately after injury or during the early stages of HS/R. The invention also contemplates administering HB-EGF to subjects at risk for HS or HS/R, such as those subjects scheduled for surgery or particularly for gastrointestinal tissue transplant, whereby administration provides an effective endogenous amount of HB-EGF at onset of HS or HS/R. Exemplary HS- or HS/R-induced injuries that may be treated, prevented or reduced by the methods of the invention are destruction of the gut mucosal barrier and deterioration of the villous microcirculatory blood flow to the intestine.

The experiments described in Example 2 used histological analysis to evaluate HS- and HS/R-induced intestinal injury. Intestinal injury was observed immediately after HS and increased as the time after resuscitation increased. In addition, intestinal injury was evaluated by measuring the number of incompetent non-healed villi per cross section on injured intestine (see Example 3). The invention provides for methods of protecting a human subject at risk for or suffering from HS- or HS/R-induced intestinal injury comprising administering a HB-EGF product to the human subject in an amount effective to protect the intestine of the human subject from injury.

Preferably, for all the methods of the invention, the HB-EGF product is a polypeptide having the amino acid sequence of SEQ ID NO: 2 or a fragment thereof that competes with HB-EGF for binding to the ErbB-1 receptor and has ErbB-1 agonist activity. A preferred HB-EGF product is human HB-EGF(74-148). In preferred embodiments, the HB-EGF product is administered in any of the methods of the invention immediately after HS or HS/R or shortly after HS or HS/R such as within about 1, about 2, about 3, about 4 or about 5 hours after resuscitation. However, the invention provides for methods of administering a HB-EGF product at any time during or after HS or HS/R has developed, such as later than about 5 hours after injury or later than about 5 hours after HS or HS/R has developed. For example, the invention contemplates administering a HB-EGF product to subjects seeking treatment several or many hours after injury or after HS has developed, or in cases where treatment is delayed for some reason. In addition, it is preferred that the HB-EGF product be administered before ischemia, hypoxia or necrotizing enterocolitis takes effect.

The experiments in Example 4 analyze in vivo villous microcirculatory blood flow in rats subjected to HS followed by variable times of reperfusion. The average microvascular villous blood flow area of HS and HS/R rats treated with a HB-EGF product was analyzed using FITC-labeled dextran. Microvascular blood flow was significantly reduced one hour after HS/R and was further reduced three hours after HS/R. The invention provides for methods of preventing or reducing HS- or HS/R-induced intestinal injury in a human subject at risk for or suffering from HS or HS/R comprising administering a HB-EGF product in an amount effective to inhibit deterioration of villous microcirculatory blood flow, e.g., to minimize the HS- or HS/R-induced decline in distribution, volume or pressure of blood in the villous microcirculation, and preferably to improve or enhance these parameters.

The villous microcirculatory blood flow analysis described in Example 4 also demonstrated that administration of a HB-EGF product to the HS and HS/R rats exhibited increased microcirculatory blood flow. The invention further provides for methods of increasing blood flow to the intestine of a human subject at risk for or suffering from HS or HS/R comprising administering HB-EGF in an amount effective to increase blood flow to the intestine. In particular, the methods of the invention will increase mesenteric blood flow.

Experiments using HB-EGF knock out (KO) mice demonstrated that HB-EGF preserved viable intestinal endothelial cells after ischemia/reperfusion (I/R) (see Example 5). In addition, the experiments in Example 6 demonstrate that HB-EGF acts as a potent vasodilator of mesenteric arterioles. The invention provides for methods of promoting angiogenesis in the intestine of a human subject at risk for or suffering from HS or HS/R comprising administering a HB-EGF product in an amount effective to protect intestinal endothelial cells from injury during or after HS or HS/R. In particular, angiogenesis is promoted by protecting intestinal endothelial cells from injury early after HS or HS/R, such as by administering HB-EGF product within about 1, about 2, about 3, about 4 or about 5 hours after HS or HS/R. Angiogenesis may also be promoted by HB-EGF-induced endothelial cell migration during or after HS or HS/R.

The invention also provides for methods of protecting microvillus architecture in a human subject at risk for or suffering from HS or HS/R comprising administering a HB-EGF product in an amount effective to preserve the intestinal microvasculature of the human subject. The invention also provides for methods in which the intestinal microvasculature is preserved due to vasodilatation induced by the HB-EGF product.

The data presented in Example 6 demonstrates that HB-EGF acts as a vasodilator. The invention provides for methods of preserving blood flow in a human subjects at risk for or suffering from intestinal injury comprising administering HB-EGF in an amount effective to promote vasodilatation of intestinal blood vessels, such as the blood vessels within the intestinal microvasculature. In particular, the invention provides for methods of preserving blood flow in a human at risk for or suffering from intestinal injury caused by HS or HS/R.

The invention also provides for methods of improving the clinical outcome of a human subject at risk for or suffering from HS or HS/R comprising administering a HB-EGF product in an amount effective to protect the intestine of the human subject from HS- or HS/R-induced intestinal injury.

The methods of the invention may be carried out in any human subject at risk for or suffering from shock, HS or HS/R. The invention contemplates treating human subjects of any age including infants, children and adults. HS may be the result of any type of injury, severe hemorrhaging, trauma, surgery, spontaneous hemorrhaging, or intestinal tissue grafting. HS causes hypotension with decreased blood flow to vital organs. Other conditions causing hypotension, although not strictly due to blood loss, may also benefit from treatment with a HB-EGF product, for example, patients with major burns, shock due to sepsis or other causes, and major myocardial infarction to name a few. In certain embodiments, the methods of the invention may be carried out in any human subject other than a subject suffering from necrotizing enterocolitis.

HB-EGF Polypeptide

The cloning of a cDNA encoding human HB-EGF (or HB-EHM) is described in Higashiyama et al., *Science*, 251: 936-939 (1991) and in a corresponding international patent application published under the Patent Cooperation Treaty as International Publication No. WO 92/06705 on Apr. 30, 1992. Both publications are hereby incorporated by reference herein in their entirety. In addition, uses of human HB-EGF are taught in U.S. Pat. No. 6,191,109, also incorporated by reference in its entirety.

The sequence of the protein coding portion of the cDNA is set out in SEQ ID NO: 1 herein, while the deduced amino acid sequence is set out in SEQ ID NO: 2. Mature HB-EGF is a secreted protein that is processed from a transmembrane precursor molecule (pro-HB-EGF) via extracellular cleavage. The predicted amino acid sequence of the full length HB-EGF precursor represents a 208 amino acid protein. A span of hydrophobic residues following the translation-initiating methionine is consistent with a secretion signal sequence. Two threonine residues (Thr75 and Thr85 in the precursor protein) are sites for O-glycosylation. Mature HB-EGF consists of at least 86 amino acids (which span residues 63-148 of the precursor molecule), and several microheterogeneous forms of HB-EGF, differing by truncations of 10, 11, 14 and 19 amino acids at the N-terminus have been identified. HB-EGF contains a C-terminal EGF-like domain (amino acid residues 30 to 86 of the mature protein) in which the six cysteine residues characteristic of the EGF family members are conserved and which is probably involved in receptor binding. HB-EGF has an N-terminal extension (amino acid residues 1 to 29 of the mature protein) containing a highly hydrophilic stretch of amino acids to which much of its ability to bind heparin is attributed. Besner et al., *Growth Factors*, 7: 289-296 (1992), which is hereby incorporated by reference herein, identifies residues 20 to 25 and 36 to 41 of the mature HB-EGF protein as involved in binding cell surface heparin sulfate and indicates that such binding mediates interaction of HB-EGF with the EGF receptor.

As used herein, "HB-EGF product" includes HB-EGF proteins comprising about amino acid 63 to about amino acid 148 of SEQ ID NO: 2 (HB-EGF(63-148)); HB-EGF proteins comprising about amino acid 73 to about amino acid 148 of SEQ ID NO: 2 (HB-EGF(73-148)); HB-EGF proteins comprising about amino acid 74 to about amino acid 148 of SEQ ID NO: 2 (HB-EGF(74-148)); HB-EGF proteins comprising about amino acid 77 to about amino acid 148 of SEQ ID NO: 2 (HB-EGF(77-148)); HB-EGF proteins comprising about amino acid 82 to about amino acid 148 of SEQ ID NO: 2 (HB-EGF(82-148)); HB-EGF proteins comprising a continuous series of amino acids of SEQ ID NO: 2 which exhibit less than 50% homology to EGF and exhibit HB-EGF biological activity, such as those described herein; fusion proteins comprising the foregoing HB-EGF proteins; and the foregoing HB-EGF proteins including conservative amino acid substitutions. In a specific embodiment, the HB-EGF product is human HB-EGF(74-148). Conservative amino acid substitutions are understood by those skilled in the art. The HB-EGF products may be isolated from natural sources known in the art (e.g., the U-937 cell line (ATCC CRL 1593)), chemically synthesized, or produced by recombinant techniques such as disclosed in WO92/06705, supra, the disclosure of which is hereby incorporated by reference. In order to obtain HB-EGF products of the invention, HB-EGF precursor proteins may be proteolytically processed in situ. The HB-EGF products may be post-translationally modified depending on the cell chosen as a source for the products.

The HB-EGF products of the invention are contemplated to exhibit one or more biological activities of HB-EGF, such as those described in the experimental data provided herein or any other HB-EGF biological activity known in the art. One such biological activity is that HB-EGF products compete with HB-EGF for binding to the ErbB-1 receptor and has ErbB-1 agonist activity. In addition, the HB-EGF products of the invention may exhibit one or more of the following biological activities: cellular mitogenicity, cellular chemoattractant, endothelial cell migration, acts as a pro-survival factor (protects against apoptosis), decrease inducible nitric oxide synthase (iNOS) and nitric oxide (NO) production in epithelial cells, decrease nuclear factor-κB (NF-κB) activation, increase eNOS (endothelial nitric oxide synthase) and NO production in endothelial cells, stimulate angiogenesis and promote vasodilatation.

The present invention provides for the HB-EGF products encoded by the nucleic acid sequence of SEQ ID NO: 1 or fragments thereof including nucleic acid sequences that hybridize under stringent conditions to the complement of the nucleotides sequence of SEQ ID NO: 1, a polynucleotide which is an allelic variant of any SEQ ID NO: 1; or a polynucleotide which encodes a species homolog of SEQ ID NO: 2.

The HB-EGF products may also be encoded by nucleotide sequences that are substantially equivalent to the polynucleotides recited above. Polynucleotides according to the invention can have at least, e.g., 65%, 70%, 75%, 80%, 81%, 82%, 83%, 84%, 85%, 86%, 87%, 88%, or 89%, more typically at least 90%, 91%, 92%, 93%, or 94% and even more typically at least 95%, 96%, 97%, 98% or 99% sequence identity to the polynucleotides recited above. Preferred computer program methods to determine identity and similarity between two sequences include, but are not limited to, the GCG program package, including GAP (Devereux et al., *Nucl. Acid. Res.*, 12: 387, 1984; Genetics Computer Group, University of Wisconsin, Madison, Wis.), BLASTP, BLASTN, and FASTA (Altschul et al., *J. Mol. Biol.*, 215: 403-410, 1990). The BLASTX program is publicly available from the National Center for Biotechnology Information (NCBI) and other sources (BLAST Manual, Altschul et al. NCB/NLM/NIH Bethesda, Md. 20894; Altschul et al., supra). The well known Smith Waterman algorithm may also be used to determine identity.

Included within the scope of the nucleic acid sequences of the invention are nucleic acid sequence fragments that hybridize under stringent conditions to SEQ ID NO: 1, or compliments thereof, which fragment is greater than about 5 nucleotides, preferably 7 nucleotides, more preferably greater than 9 nucleotides and most preferably greater than 17 nucleotides. Fragments of, e.g., 15, 17, or 20 nucleotides or more that are selective for (i.e., specifically hybridize to any one of the polynucleotides of the invention) are contemplated.

The term "stringent" is used to refer to conditions that are commonly understood in the art as stringent. Hybridization stringency is principally determined by temperature, ionic strength, and the concentration of denaturing agents such as formamide. Examples of stringent conditions for hybridization and washing are 0.015 M sodium chloride, 0.0015 M sodium citrate at 65-68° C. or 0.015 M sodium chloride, 0.0015M sodium citrate, and 50% formamide at 42° C. See Sambrook et al., *Molecular Cloning: A Laboratory Manual*, 2nd Ed., Cold Spring Harbor Laboratory, (Cold Spring Harbor, N.Y. 1989). More stringent conditions (such as higher temperature, lower ionic strength, higher formamide, or other denaturing agent) may also be used, however, the rate of hybridization will be affected. In instances wherein hybridization of deoxyoligonucleotides is concerned, additional exemplary stringent hybridization conditions include washing in 6×SSC 0.05% sodium pyrophosphate at 37° C. (for 14-base oligos), 48° C. (for 17-base oligos), 55° C. (for 20-base oligos), and 60° C. (for 23-base oligos).

Other agents may be included in the hybridization and washing buffers for the purpose of reducing non-specific and/or background hybridization. Examples are 0.1% bovine serum albumin, 0.1% polyvinyl-pyrrolidone, 0.1% sodium pyrophosphate, 0.1% sodium dodecylsulfate, NaDodSO4, (SDS), ficoll, Denhardt's solution, sonicated salmon sperm DNA (or other non-complementary DNA), and dextran sulfate, although other suitable agents can also be used. The concentration and types of these additives can be changed without substantially affecting the stringency of the hybridization conditions. Hybridization experiments are usually carried out at pH 6.8-7.4, however, at typical ionic strength conditions, the rate of hybridization is nearly independent of pH. See Anderson et al., *Nucleic Acid Hybridisation: A Practical Approach*, Ch. 4, IRL Press Limited (Oxford, England). Hybridization conditions can be adjusted by one skilled in the art in order to accommodate these variables and allow DNAs of different sequence relatedness to form hybrids.

The HB-EGF products of the invention include, but are not limited to, a polypeptide comprising: the amino acid sequences encoded by the nucleotide sequence of SEQ ID NO: 1, or the corresponding full length or mature protein. Polypeptides of the invention also include polypeptides preferably with HB-EGF biological activity described herein that are encoded by: (a) an open reading frame contained within the nucleotide sequences set forth as SEQ ID NO: 1, preferably the open reading frames therein or (b) polynucleotides that hybridize to the complement of the polynucleotides of (a) under stringent hybridization conditions.

The HB-EGF products of the invention also include biologically active variants of the amino acid of SEQ ID NO: 2; and "substantial equivalents" thereof with at least, e.g., about 65%, about 70%, about 75%, about 80%, about 85%, 86%, 87%, 88%, 89%, at least about 90%, 91%, 92%, 93%, 94%, typically at least about 95%, 96%, 97%, more typically at least about 98%, or most typically at least about 99% amino acid identity) that retain HB-EGF biological activity. Polypeptides encoded by allelic variants may have a similar, increased, or decreased activity compared to polypeptides having the amino acid sequence of SEQ ID NO: 2.

The HB-EGF products of the invention include HB-EGF polypeptides with one or more conservative amino acid substitutions that do not affect the biological activity of the polypeptide. Alternatively, the HB-EGF polypeptides of the invention are contemplated to have conservative amino acids substitutions which may or may not alter biological activity. The term "conservative amino acid substitution" refers to a substitution of a native amino acid residue with a nonnative residue, including naturally occurring and nonnaturally occurring amino acids, such that there is little or no effect on the polarity or charge of the amino acid residue at that position. For example, a conservative substitution results from the replacement of a non-polar residue in a polypeptide with any other non-polar residue. Further, any native residue in the polypeptide may also be substituted with alanine, according to the methods of "alanine scanning mutagenesis". Naturally occurring amino acids are characterized based on their side chains as follows: basic: arginine, lysine, histidine; acidic: glutamic acid, aspartic acid; uncharged polar: glutamine, asparagine, serine, threonine, tyrosine; and non-polar: phenylalanine, tryptophan, cysteine, glycine, alanine, valine, proline, methionine, leucine, norleucine, isoleucine.

Hemorrhagic Shock

Shock is a state of inadequate perfusion, which does not sustain the physiologic needs of organ tissues. Hemorrhagic shock (HS) refers to shock that is caused by blood loss that exceeds the ability of the body to compensate and to provide adequate tissue perfusion and oxygenation. HS is frequently is caused by trauma, but also may be caused by spontaneous hemorrhage (e.g., GI bleeding, childbirth), surgery, and other causes. Frequently, an acute bleeding episode will cause HS, but HS may also occur in chronic conditions with subacute blood loss.

Untreated HS can lead to death. Without intervention, a classic trimodal distribution is seen in severe HS. An initial peak of mortality occurs within minutes of hemorrhage due to immediate exsanguination. Another peak occurs after 1 to several hours due to progressive decompensation. A third peak occurs days to weeks later due to sepsis and organ failure. Therefore, the methods of the invention preferably are carried out during the early stages of HS such as after or during the initial peak, or before or during the second peak (1 to several hours after the initial hemorrhage).

A person in shock has extremely low blood pressure. Depending on the specific cause and type of shock, symptoms will include one or more of the following: anxiety, agitation, confusion, pale, cool and clammy skin, low or no urine production, bluish lips and fingernails, dizziness, light-headedness, faintness, profuse sweating, rapid but weak pulse, shallow breathing, chest pain and unconsciousness.

Resuscitation during or after HS/R is known to have deleterious effects on the blood vessels of the patient. For example, HS/R is characterized by progressive deterioration of mesenteric blood flow. In addition, progressive intestinal hypoperfusion after HS/R contributes to loss of the gut mucosal barrier and to hypoxia-induced intestinal inflammation, both of which are critical to the initiation of MODS after HS/R.

The Role of HB-EGF in Intestinal Cytoprotection

Induction and activation of the EGF receptor have been demonstrated in different tissues, including the intestines, during hypoxia and after ischemia. (Ellis et al., *Biochem. J.* 354:99-106, 2001; Lin et al., *J Lab Clin Med;* 125:724-33, 1995; Nishi et al., *Cancer Res* 62:827-34, 2002; Sondeen et al., *J Lab Clin Med* 134:641-8, 1999; Yano et al., *Nephron* 81:230-3, 1999). Previous studies have shown that HB-EGF mRNA and protein are induced after exposure of intestinal epithelial cells to anoxia/reoxygenation (A/R) in vitro, and after intestinal I/R injury in vivo. (Xia et al., *J Invest Surg* 16:57-63, 2003). Hypoxia and I/R have been found to induce HB-EGF transcription and protein synthesis in different tissues including the brain and kidney. (Homma et al., *J Clin Invest* 96:1018-25, 1995; Jin et al., *J Neurosci* 22:5365-73, 2002; Kawahara et al., *J Cereb Blood Flow Metab* 19:307-20, 1999; Sakai et al., *J. Clin. Invest.;* 99:2128-2138, 1997). During the early phases of hypoxia and oxidative stress, activation of EGFR and shedding of proHB-EGF occur, leading to immediate availability of soluble HB-EGF protein for targeting via autocrine or paracrine pathways. HB-EGF shedding is followed by the induction of transcription and de novo synthesis of HB-EGF (El-Assal et al., *Semin Pediatr Surg* 13:2-10, 2004).

Intestinal epithelium undergoes a dynamic and continuous process of renewal and replacement with a turnover time of 3-6 days. (Potten et al., *Am J Physiol* 273:G253-7, 1997). Depending more on the depth of injury rather than the total surface area affected, the process of healing starts as early as a few minutes after injury (Ikeda et al., *Dig Dis Sci* 2002; 47:590-601, 2002). The most important priority during intestinal regeneration is reconstitution of epithelial cell continuity, allowing restoration of barrier function and prevention of systemic toxic complications. This is achieved by rapid epithelial cell migration from the wound edge, a process known as "restitution" (Ikeda et al., *Dig Dis Sci* 47:590-601, 2002; McCormack et al., *Am J Physiol;* 263:G426-35, 1992; Moore et al. *Am J Physiol* 257:G274-83, 1989; Moore et al. *Gastroenterology* 102:119-30, 1992). Early migration of goblet cells, which are more resistant to ischemia-induced cell death than enterocytes, serves as a source of both cell lining and mucous secretion, thus promoting rapid recovery of intestinal barrier function (Ikeda et al., *Dig Dis Sci* 47:590-601, 2002). Complete intestinal repair is achieved by proliferation and differentiation of crypt epithelium, which does not occur as early as restitution. Following administration of HB-EGF to rats exposed to intestinal I/R, a significant improvement in intestinal healing characterized by reduced mucosal damage was observed (Pillai et al., *J Surg Res* 87:225-31, 1999). The early phase of intestinal healing HB-EGF was shown to induce intestinal restitution (El-Assal et al., *Gastroenterology* 129:609-25, 2005) whereas in the later phase of healing HB-EGF promotes crypt cell proliferation (Xia et al., *J Pediatr Surg* 37:1081-7; 2002). In addition, the effects of HB-EGF in inducing restitution are mediated by both the PI3-kinase and MAPK intracellular signaling pathways (El-Assal et al. Gastroenterology 129:609-25, 2005). HB-EGF administration leads to preservation of gut barrier function and intestinal permeability after intestinal I/R (El-Assal et al. *Gastroenterology* 129:609-25, 2005), with resultant decrease in bacterial translocation (Xia et al., *J Pediatr Surg* 37:1081-7; 2002). It is important to note that the protective effects of HB-EGF administration are seen even when the growth factor is administered during or after the ischemic interval has already occurred (Martin et al., *J Pediatr Surg.* 40:1741-7, 2005). Thus, prophylactic administration of HB-EGF prior to ischemia is not required. Most importantly, HB-EGF improves survival in rats exposed to intestinal I/R injury (Pillai et al., *J Surg Res* 87:225-31, 1999).

Additional studies demonstrated that treatment with HB-EGF reduced the generation of ROS in rats exposed to intestinal I/R in vivo and in leukocytes exposed to ROS-inducing stimuli in vitro (Kuhn et al., *Antioxid Redox Signal* 4:639-46, 2002). HB-EGF also preserved intestinal epithelial cell ATP levels in cells exposed to hypoxia (Pillai et al., *J. Pediatr. Surg.* 33:973-979, 1998). HB-EGF is known to downregulate expression of adhesion molecules including P- and E-selectin and intercellular adhesion molecule-1 (ICAM-1)/vascular cell adhesion molecule-1 (VCAM-1) after intestinal I/R (Xia et al., *J Pediatr Surg* 38:434-9. 2003). Downregulation of adhesion molecules was followed by reduced infiltration of leukocytes, which are critical mediators of I/R (Xia et al., J Pediatr Surg 38:434-9. 2003).

Exposure of intestinal epithelium to I/R results in cell death, with apoptosis rather than necrosis as the major mechanism of cell death. One of the unique functions of HB-EGF is its ability to protect against apoptotic cell death. sHB-EGF is known to protect enterocytes from hypoxia-induced intestinal necrosis (Pillai et al., *J. Pediatr. Surg.* 33:973-979, 1998) and from pro-inflammatory cytokine-induced apoptosis (Michalsky et al., *J Pediatr Surg* 36:1130-5. 2001) in vitro. HB-EGF is also known to act as a pro-survival factor in cells exposed to various forms of stress including mechanical stress, serum starvation and exposure to cytotoxic agents. Recent studies have demonstrated that HB-EGF decreases intestinal epithelial cell apoptosis in vivo in a rat model of necrotizing enterocolitis (Feng et al., *J Pediatr Surg* 2006 (in press).

Nitric oxide (NO) is another mediator of I/R-induced apoptosis and intestinal mucosal damage. Despite the protective effect of constitutive NO, there is ample evidence that high levels of NO induce apoptosis and mediate tissue damage in different cell types including intestinal epithelial cells during I/R. iNOS (inducible nitric oxide synthase) inhibitors led to attenuated NO production and decreased hypoxia-induced intestinal apoptosis with preservation of gut barrier function in rats with endotoxemia. Furthermore, iNOS knock-out mice are more resistant to intestinal I/R-induced mucosal injury. Collectively, these studies clearly indicate that reduction of iNOS can decrease I/R-induced intestinal damage. HB-EGF downregulates cytokine-induced iNOS and NO production in intestinal epithelial cells in vitro, and I/R-induced intestinal iNOS expression and serum NO levels in vivo. HB-EGF has been shown to decrease iNOS and NO production in intestinal epithelial cells that is dependent upon its ability to decrease nuclear factor-κB (NF-κB) activation in a PI3-kinase dependent fashion. Reduction of I/R-induced overproduction of NO in IEC represents an additional cytoprotective mechanism of HB-EGF.

HB-EGF is a hypoxia- and stress-inducible gene that is involved in reduction of I/R-induced tissue damage. It promotes structural recovery after I/R by enhancing cell proliferation and by inducing migration of healthy epithelial cells from the edge of damaged tissues. In addition to promoting healing based on its positive trophic effects, HB-EGF also protects the intestine by decreasing leukocyte infiltration and production of injurious mediators after injury, thus protecting epithelial cells from apoptosis and necrosis. It is likely that reducing I/R-induced IEC death will ameliorate intestinal damage and reduce systemic complications.

HB-EGF and Angiogenesis

Angiogenesis, the formation of new blood vessels, is an essential part of both normal developmental processes and many pathologic processes, ranging from organ growth in the embryo to repair of wounded tissue in the adult. In response to a stimulus from an angiogenic growth factor, endothelial cells migrate into the interstitial space by first degrading the underlying basement membrane. Behind the front of migrating cells, other endothelial cells continuously proliferate to provide the necessary number of cells needed to generate the new vessel (neoangiogenesis). Angiogenesis is a critical event in wound healing, and angiogenic growth factors are key to the initiation of angiogenesis and maintenance of the vascular network.

Vascular endothelial growth factor (VEGF) and basic fibroblast growth factor (bFGF) are potent angiogenic growth factors. However, there is growing evidence that HB-EGF may also be a potent stimulator of angiogenesis (Ushiro et al., *Jpn. J. Cancer Res.* 87:68-77, 1996; Abramovitch et al., *FEBS Lett.* 425:441-447, 1998). HB-EGF is expressed in endothelial cells and is also induced by VEGF. HB-EGF was found to enhance neurogenesis and angiogenesis after focal cerebral ischemia in rats (Sugiura et al., *Stroke* 36:859-64, 2005). The data provided in Examples 5 and 6 demonstrates that HB-EGF protects EC and preserves microvascular blood flow after intestinal I/R injury.

Pharmaceutical Compositions

The administration of HB-EGF products is preferably accomplished with a pharmaceutical composition comprising an HB-EGF product and a pharmaceutically acceptable carrier. The carrier may be in a wide variety of forms depending on the route of administration. Suitable liquid carriers include saline, PBS, lactated Ringer solution, human plasma, human albumin solution, 5% dextrose and mixtures thereof. The route of administration may be oral, rectal, parenteral, or through a nasogastric tube. Examples of parenteral routes of administration are intravenous, intra-arterial, intraperitoneal, intraluminally, intramuscular, intragastrically or subcutaneous injection or infusion. The presently preferred route of administration is the oral route as the present invention contemplates that the acid stability of HB-EGF is a unique factor as compared to, for example, EGF. The HB-EGF pharmaceutical composition may also include other ingredients to aid solubility, or for buffering or preservation purposes. Pharmaceutical compositions containing HB-EGF products comprise HB-EGF at a concentration of about 0.05 to 10 mg/ml and preferably at a concentration of 1 mg/ml in saline. Suitable doses are in the range from 0.5-1000 µg/kg, e.g., 1-10 µg/kg or 600-800 µg/kg. A preferred dose is 600 µg/kg administered intravenously once a day. Additional preferred doses may be administered once, twice, three, four, five or six times a day either enterally or intravenously. The HB-EGF may be administered as a bolus, either once at the onset of therapy or at various time points during the course of therapy, such as every four hours, or may be infused for instance at the rate of about 0.01 µg/kg/h to about 5 µg/kg/h during the course of therapy until the patient shows signs of clinical improvement. Addition of other bioactive compounds [e.g., antibiotics, free radical scavenging or conversion materials (e.g., vitamin E, beta-carotene, BHT, ascorbic acid, and superoxide dimutase), fibrolynic agents (e.g., plasminogen activators), and slow-release polymers] to the HB-EGF compounds or separate administration of the other bioactive compounds is also contemplated.

DETAILED DESCRIPTION

The following examples illustrate the invention wherein Example 1 describes a rat model of hemorrhagic shock and resuscitation, Example 2 demonstrates that HB-EGF decreases intestinal histologic damage after HS/R, Example 3 demonstrates that HB-EGF preserves the structural intestinal barrier after HS/R, Example 4 demonstrates that HB-EGF improves mesenteric blood flow after HS/R, Example 5 demonstrates that HB-EGF preserves EC after intestinal I/R injury and Example 6 demonstrates that HB-EGF is a potent vasodilator of the intestinal microvasculature.

EXAMPLE 1

Rat Model of Hemorrhagic Shock and Resuscitation

All procedures were approved by the Institutional Animal Care and Use Committee of the Children's Research Institute. Adult male pathogen-free Sprague-Dawley rats weighing 250-300 g were used after acclimatization for 72 hours. Animals were fasted overnight with access to water only prior to surgery. Under inhalation anesthesia using 2% isoflurane, the right carotid artery was canulated using a PE-50 catheter connected to a three way stopcock for monitoring of mean arterial blood pressure (MAP) and heart rate as well as blood withdrawal. Cannulae and syringes were flushed with heparinized saline (1000 U/ml). Shock was produced by gradual blood withdrawal over 15 minutes to achieve a mean arterial blood pressure of 45 mmHg. MAP was maintained at that level for 90 minutes, with continuous monitoring of blood pressure, and blood withdrawal or fluid infusion as needed. Resuscitation was then achieved by gradual reperfusion of the withdrawn blood in addition to lactated Ringer's solution to achieve a MAP of $\geq 85\%$ of the pre-shock level.

Rats were divided into three groups: 1) HS/R+HB-EGF group (HS/R+HB-EGF), which received a single bolus intra-arterial injection of rHB-EGF (600 µg/kg) at the onset of resuscitation, 2) HS/R group, which received an identical intra-arterial injection of vehicle (0.1% bovine serum albumin in phosphate buffer saline) only, and 3) control group, subjected to identical procedures without blood withdrawal. Throughout the procedure the animal's body temperature was maintained at 37° C. All animals recovered completely from the initial operative procedure. Three rats were used per group, with each experiment performed in duplicate. For analysis, animals were euthanized under anesthesia. All experiments utilized human rHB-EGF corresponding to amino acids 74-148 of the mature HB-EGF protein that was produced by recombinant DNA technology and purified as previously described in Davis et al. (*Protein Expr. Purif.* 8(1):57-67, 1996)

EXAMPLE 2

HB-EGF Decreases Intestinal Histologic Damage after HS/R

There were no significant differences in MAP among different animals before HS or after resuscitation. To measure the histology injury score, the distal 5 cm of ileum rats suffering from HS was harvested immediately upon sacrifice and specimens were paraffin embedded. Tissue sections were deparaffinized, rehydrated, and stained with hematoxylin and eosin (H&E). Histological scoring of the depth of tissue injury was performed according to Chiu et al. (*Arch. Surg.* 101(4):478-83, 1970), with modifications as follows: score 0, no damage; score 1, subepithelial space at the villous tip; score 2, loss of mucosal lining of the villous tip; score 3, loss of less than half of the villous structure; score 4, loss of more than half of the villous structure; and score 5, transmural necrosis. Sections were evaluated blindly without prior knowledge of animal background.

HS-induced intestinal histological injury was compatible to that previously observed after SMAO. Immediately after HS, the average histological injury score was 1.6±0.41. In HS/R rats, this increased to 2.5±0.5 one hour after resuscitation, and increased further to 3.08±0.51 three hours after resuscitation, the latter being significantly higher than the depth of injury immediately after HS (p<0.05), indicating that HS-induced intestinal injury progressively increases after resuscitation.

In HS/R+HB-EGF rats, the average depth of intestinal injury was 1.8±0.71 one hour after resuscitation and 2.0±0.5 3 hours after resuscitation. In these rats, the post-resuscitation intestinal injury scores were not significantly different from the injury score at the end of HS. However, the injury score in HS/R+HB-EGF rats was significantly lower than that in HS/R rats three hours after resuscitation (p<0.05), indicating that HB-EGF treatment protected the intestine from resuscitation-induced intestinal injury.

EXAMPLE 3

HB-EGF Preserves the Structural Intestinal Barrier after HS/R

Quantification of incompetent villi was used to evaluate the structural intestinal barrier as previously described. (El-Assal et al. *Gastroenterology* 129(2):609-25, 2005) An incompetent villous was identified as a villous with an incomplete mucosal lining, regardless of the depth of injury. Any epithelial gap was considered as a potential port of bacterial or macromolecular translocation into the submucosal space, and hence was considered a breach in the intestinal barrier. The number of incompetent villi reflects both the functional integrity of the intestinal barrier as well as early healing by restitution. The degree of in vivo restitution was evaluated using the criteria set out in El-Assal et al. These criteria are applied to well-aligned villi in PAS-stained sections and include: 1) histologic features indicative of prior loss of mucosa resulting in subsequent villous contraction, with short, blunted, or concave villous tips compared to non-damaged or less injured villi in the same histologic section; 2) restoration of the mucosal surface of injured villi with a single layer of flat, squamous enterocytes resulting from migration and flattening during restitution; and/or 3) restoration of mucosal continuity with a single cell layer containing four or more goblet cells in continuity, without intervening enterocytes. The average numbers of incompetent villi per cross section were quantified as an indicator of intestinal restitution.

At the end of HS, the average number of incompetent non-healed villi per cross section was 11.3±4.5. The number of incompetent villi in HS/R rats increased to 39.9±17 one hour after resuscitation and to 31.7±6.4 three hours after resuscitation, the latter being significantly higher than that at the end of HS (p<0.05). In HS/R+HB-EGF rats, the number of incompetent villi was 9.9±4.4 one hour after resuscitation, and 9.08±4.3 three hours after resuscitation, both significantly lower than that in HS/R rats. This indicates that HB-EGF protects against resuscitation-induced destruction of the gut mucosal barrier.

EXAMPLE 4

HB-EGF Improves Mesenteric Blood Flow after HS/R

Villous microcirculatory blood flow was evaluated in vivo according to the method of Stappenbeck et al. (*Proc. Natl. Acad. Sci. USA* 99(24):15451-5, 2002) with some modifications. Rats were subjected to HS for 90 minutes followed by variable periods of reperfusion. High molecular weight (FD2000) flourescein isothiocyanate-labeled (FITC) dextran (500 µl of a 10 mg/ml solution, Sigma, St. Louis, Mo.) was injected into the carotid artery 5 minutes prior to sacrifice. An 8 cm segment of distal small bowel was excised, perfused with fixation solution containing 0.5% paraformaldehyde, 15% picric acid, and 0.1 M sodium phosphate buffer (pH 7.0), and shaken gently at 4° C. for 12 hours in fixation solution. Specimens were rinsed in ice-cold PBS (three washes, 5 minutes each), followed by a 3 hour incubation in 10% sucrose/PBS (4° C.) and an overnight incubation in 20% sucrose/10% glycerol/PBS (4° C.).

Intestinal segments were frozen in OCT compound and 60 µm-thick sections were cut across the cephalocaudal axis. Sections were air-dried for 2 hours at room temperature (RT) in the dark, followed by rehydration in ice-cold PBS (1 minute) and overnight incubation at 4° C. in 3% deoxycholic acid (Sigma). Sections were rinsed twice in water (5 minutes each at room temperature), and once in PBS (5 minutes at room temperature) to remove residual deoxycholic acid. Intestinal epithelial cells (IEC) were stained by incubating sections in a 1:1000 solution of Syto61 (Molecular Probes, Carlsbad, Calif.) for 1 hour at room temperature, followed by three PBS washes (5 minutes each at room temperature). Sections were mounted in 50% glycerol/PBS and stored at 4° C. Cryosections were viewed with an LSM 510 confocal microscope (Zeiss, Thornwood, N.Y.) and scanned at 5 µm-thick intervals. Scans were projected in three dimensions by taking 8-10 serial images, aligning them at 7-10° intervals, and compiling/rotating them about the y axis using LSM 510 software (Zeiss).

The extent of microvascular perfused area was quantified using MetaMorph computer software. Scanned images were processed to separate the green channel representing the perfused area and the red channel representing epithelial cell staining. The extent of green staining per section was indicative of the perfused area %. Three rats were used per group, with each experiment performed in duplicate. At least 5 sections were evaluated per animal.

The average microvasular villous blood flow area % was 3.9±0.35% prior to HS (basal flow). Microvascular blood flow was significantly reduced to 2.6±0.46% in HS/R rats one hour after resuscitation compared to basal pre-HS levels (p<0.05) and to 2.9±0.63% three hours after resuscitation. This indicated that HS/R resulted in significant deterioration in microvascular flow with vasoconstriction of the villous vasculature, consistent with previous studies (Zakaria et al. *Am J Surg* 186(5):443-8, 2003; Fruchterman et al. *Shock* 10(6):417-22, 1998).

Treatment with HB-EGF not only prevented HS/R-induced deterioration of villous microcirculatory blood flow, but actually resulted in increased flow compared to basal levels. In HS/R+HB-EGF rats, the average microvascular villous blood flow area % was 4.5±0.43% 1 hour after resuscitation, which was significantly higher than that in HS/R rats at this time point (p<0.05). Three hours after resuscitation the villous microcirculatory perfused area % in HS/R+HB-EGF rats increased to 8.04±1.5%, which was significantly higher than that in HS/R rats at this time point, and significantly higher than basal pre-HS levels (p<0.05).

EXAMPLE 5

HB-EGF Preserves Endothelial Cells After Intestinal I/R Injury

An additional possible mechanism by which HB-EGF might promote angiogenesis after I/R is via protection of EC from injury after the initial insult. To investigate the role of HB-EGF in preservation of viable EC, intestine from HB-EGF knock-out (KO) and wild type (WT) mice was examined by IHC using anti-von Willebrand factor (VWF) antibodies to stain EC (Jackson et al. *Embo J* 22: 2704-2716, 2003). After exposure to I/R injury, HB-EGF KO mice have significantly decreased EC staining compared to WT mice. Similar results were obtained using anti-CD34 and anti-αSMA. Thus, HB-EGF protects EC from injury after intestinal I/R. This may leave a population of viable EC available for prompt initiation of angiogenesis after I/R.

EXAMPLE 6

HB-EGF is a Potent Vasodilator of the Intestinal Microvasculature

Preservation of blood flow after intestinal injury is a major determinant of subsequent tissue viability, and is dependent upon flow through the main resistance vessels, the terminal mesenteric arterioles. The effect of HB-EGF on the pressure and flow characteristics of freshly isolated individual porcine terminal mesenteric arterioles was examined (~200 μm). These studies demonstrate that HB-EGF acts as a potent vasodilator of mesenteric arterioles. Thus, HB-EGF protects EC and preserves the patency of the microvasculature after I/R injury, and acts as a vasodilator of the intestinal circulation as well.

It is claimed:

1. A method of reducing hemorrhagic shock (HS)-induced or hemorrhagic shock and resuscitation (HS/R)-induced intestinal injury in a human subject comprising administering a heparin binding EGF (HB-EGF) product in an amount effective to inhibit deterioration of villous microcirculatory blood flow,
wherein the HB-EGF product comprises amino acids 74 to 148 of SEQ ID NO: 2 and is administered immediately following hemorrhagic shock or within 1-5 hours after resuscitation.

2. The method of claim 1, wherein the intestinal injury is destruction of the gut mucosal barrier.

3. The method claim 1, wherein the heparin binding EGF product is administered intravenously, intraluminally or intragastrically.

4. The method of claim 1, wherein the heparin binding EGF product is administered within about 1 hour after resuscitation.

5. The method of claim 4, wherein the heparin binding EGF product is administered within about 2 hours after resuscitation.

6. The method of claim 4, wherein the heparin binding EGF product is administered within about 3 hours after resuscitation.

7. A method of increasing blood flow to the intestine of a human subject suffering from hemorrhagic shock (HS) or hemorrhagic shock and resuscitation (HS/R) comprising administering a heparin binding EGF (HB-EGF) product in an amount effective to increase blood flow to the intestine,
wherein the HB-EGF product comprises amino acids 74 to 148 of SEQ ID NO: 2.

8. The method of claim 7, wherein mesenteric blood flow is increased.

* * * * *